Figure 1:
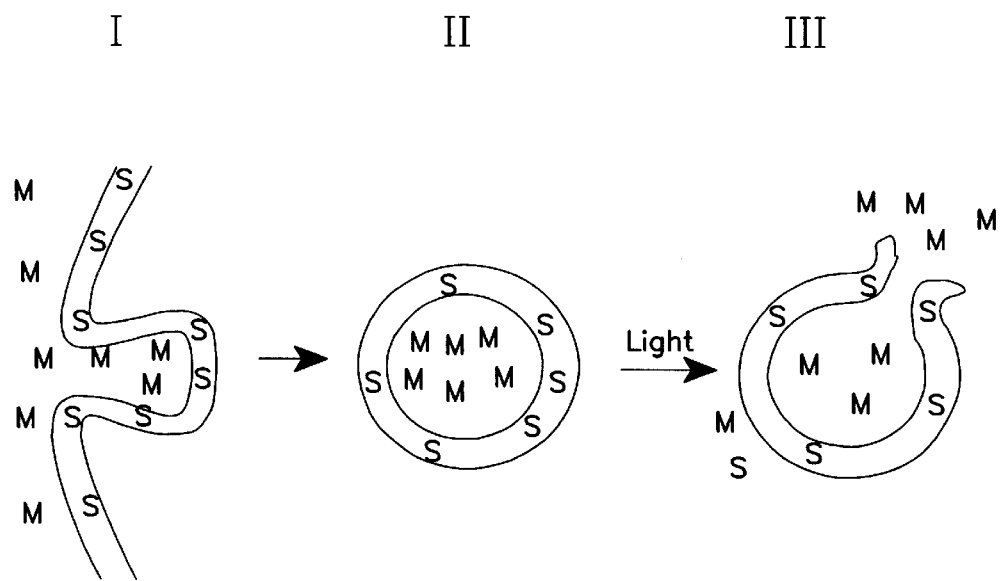

United States Patent [19]
Berg et al.

[11] Patent Number: 5,876,989
[45] Date of Patent: Mar. 2, 1999

[54] TRANSFER OF MOLECULES INTO THE CYTOSOL OF CELLS

[75] Inventors: Kristian Berg, Heggedal; Kirsten Sandvig; Johan Moan, both of Oslo, all of Norway

[73] Assignee: Photocure AS, Oslo, Norway

[21] Appl. No.: 793,794

[22] PCT Filed: Sep. 4, 1995

[86] PCT No.: PCT/NO95/00149

§ 371 Date: Mar. 28, 1997

§ 102(e) Date: Mar. 28, 1997

[87] PCT Pub. No.: WO96/07432

PCT Pub. Date: Mar. 14, 1996

[30] Foreign Application Priority Data

Sep. 8, 1994 [NO] Norway .................................... 943327

[51] Int. Cl.⁶ .................................................. C12N 13/00
[52] U.S. Cl. .................. 435/173.7; 435/375; 514/44; 514/410; 540/145; 935/52
[58] Field of Search .................. 514/44, 410; 540/145; 435/375, 173.7; 935/52

[56] References Cited

U.S. PATENT DOCUMENTS

| | | | |
|---|---|---|---|
| 4,649,151 | 3/1987 | Dougherty et al. | 514/410 |
| 5,059,619 | 10/1991 | Haeger et al. | 514/410 |
| 5,066,274 | 11/1991 | Bommer et al. | 604/20 |
| 5,095,030 | 3/1992 | Levy et al. | 514/410 |
| 5,179,120 | 1/1993 | Vogel et al. | 514/410 |

FOREIGN PATENT DOCUMENTS

| | | |
|---|---|---|
| WO 89/01630 | 2/1989 | Norway . |
| 891491 | 4/1989 | Norway . |
| 924151 | 10/1992 | Norway . |
| 173319 | 12/1993 | Norway . |
| 934837 | 12/1993 | Norway . |
| 176645 | 5/1995 | Norway . |
| 176947 | 6/1995 | Norway . |
| 176786 | 7/1995 | Norway . |
| 179410 | 10/1996 | Norway . |
| 180742 | 3/1997 | Norway . |
| 2 209 468 | 5/1989 | United Kingdom . |
| WO 90/00393 | 1/1990 | WIPO . |
| WO 93/14142 | 7/1993 | WIPO . |

OTHER PUBLICATIONS

Kopecek, J., B. Rihova and N.L. Krinick, "Targetable photoactivatable polymeric drugs", *Journal of Controlled Release* v. 16, pp. 137–144.

Primary Examiner—Bruce R. Campell
Attorney, Agent, or Firm—Merchant, Gould, Smith, Edell, Welter & Schmidt

[57] ABSTRACT

A method for releasing molecules into the cytosol of cells without killing the majority of the cells by allowing the molecules to be taken up in endosomes, lysosomes or other cell compartments and use light activation of photosensitizing compounds to rupture the membranes of the endosomes, lysosomes or other cell compartments, is described.

7 Claims, 13 Drawing Sheets

TRANSFER OF MOLECULES INTO THE CYTOSOL OF CELLS

The present invention relates to a method for introducing molecules in cells by disrupting endosomal and lysosomal membranes using photodynamic treatment, without killing the majority of the cells by the photodynamic treatment.

The majority of molecules do not readily penetrate cell membranes. Methods for introducing molecules into the cytosol of living cells are useful tools for manipulating and studying biological processes. Among the most commonly used methods today are microinjection, red blood cell ghost mediated fusion and liposome fusion, osmotic lysis of pinosomes, scrape loading, electroporation, calcium phosphate and virus mediated transfection. These techniques are useful for investigations of cells in culture, although in many cases impractical, time consuming, inefficient or they induce significant cell death. They are thus not optimal for use in biological and medical research or therapeutics in which the cells shall remain functional.

It is well known that porphyrins and many other photosensitizing compounds induce cytotoxic effects on cells and tissues. These effects are based upon the fact that the photosensitizing compound upon light exposure releases singlet $^1O_2$ which decomposes the membranes of the cells and cell structures and eventually kill the cells if the destruction is extensive. These effects have been utilized to treat several types of neoplastic diseases. The treatment is named photodynamic therapy (PDT) and is based on injection of a photosensitizing and tumorlocalizing dye followed by exposure of the tumor region to light. The cytotoxic effect is mediated mainly through the formation of singlet oxygen. This reactive intermediate has a very short lifetime in cells ($<0.04$ $\mu$s). Thus, the primary cytotoxic effect of PDT is executed during light exposure and very close to the sites of formation of $^1O_2$. $^1O_2$ reacts with and oxidize proteins (histidine, tryptophan, methionine, cysteine, tyrosine), DNA (guanine), unsaturated fatty acids and cholesterol. One of the advantages of PDT is that tissues unexposed to light will not be affected. There is extensive documentation regarding use of PDT to destroy unwanted cell population, for example neoplastic cells. Several patents relate to photodynamic compounds alone or conjugated with immunoglobulins directed to neoplastic cell receptor determinants making the complex more cell specific. Certain photochemical compounds, such as hematoporphyrin derivates have furthermore an inherent ability to concentrate in malign cells. These methods and compounds, which are directed to destroy the unwanted cells are described in the Norwegian patent NO 173319, in Norwegian patent applications Nos 90 0731, 90 2634, 90 1018, 94 1548, 85 1897, 93 4837, 92 4151 and 89 1491.

In PCT/US93/00683 a drug delivery system is described which is comprised of an anticancer drug and a photoactivatable drug attached to copolymeric carriers. Upon administration this complex enters the cell interior by pinocytosis or phagocytosis and will be located inside the endosomes and lysosomes. In the lysosomes the bond between the antineoplastic compound and the polymer is hydrolyzed and the former can diffuse passively through the lysosome membrane into cytosol. Thus this method limits the method to small molecular compounds which are able to diffuse across the lysosome membranes. After allowing a time lag for diffusion a light source of appropriate wavelength and energy is applied to activate the photoactivatable compound. The combined effect of the anticancer drug and photoactivatable drug destroy the cell. Thus all use of photoactivatable compounds known is directed to extensively destroy cell structures leading to cell death It is not known of a method to release membrane unpermeable molecules into the cytosol after localized rupturing of endosomal/lysosomal membranes.

The object of the present invention is thus to provide a method to transport molecules into cytosol of living cells, in culture or in tissues, by exposing the cells to a photoactivatable compound, the molecule(s) which is (are) to be transported into the cytosol, both of which uptake may be facilitated by various carriers, exposing the cell to light of suitable wavelength and energy to disrupt the endosomal and lysosomal membranes and release the molecules into the cytosol without destroying the functionality of the majority of the cells. The photosensitizer and the molecule(s) which is (are) to be transported into the cytosol may each be conjugated to suitable carriers, optionally facilitating the uptake of the molecules of interest.

This object is obtained by the present invention characterized by the enclosed claims.

The present invention relates to a method for transporting any molecules into the cytosol of living cells after which the molecules shall be available in the cytosol and the cell shall maintain its functionality. This is performed by exposing the cell(s) to a photoactivatable compound which is taken up by the cell and will be located in endosomes, lysosomes or other cellular compartments, conjugated to or separately together with carrier molecules, targeting immunoglobulins and the molecules to be transported into the cytosol and expose the cells to light of suitable wavelength to activate the photosensitizing compound, such that only the endosomal, lysosomal or other cellular compartment membranes are ruptured and the molecules released in the cytosol without the cell losing its functionability by the action of the photoactivated compound and possible action of the endosomal/lysosomal content.

Figure 2:
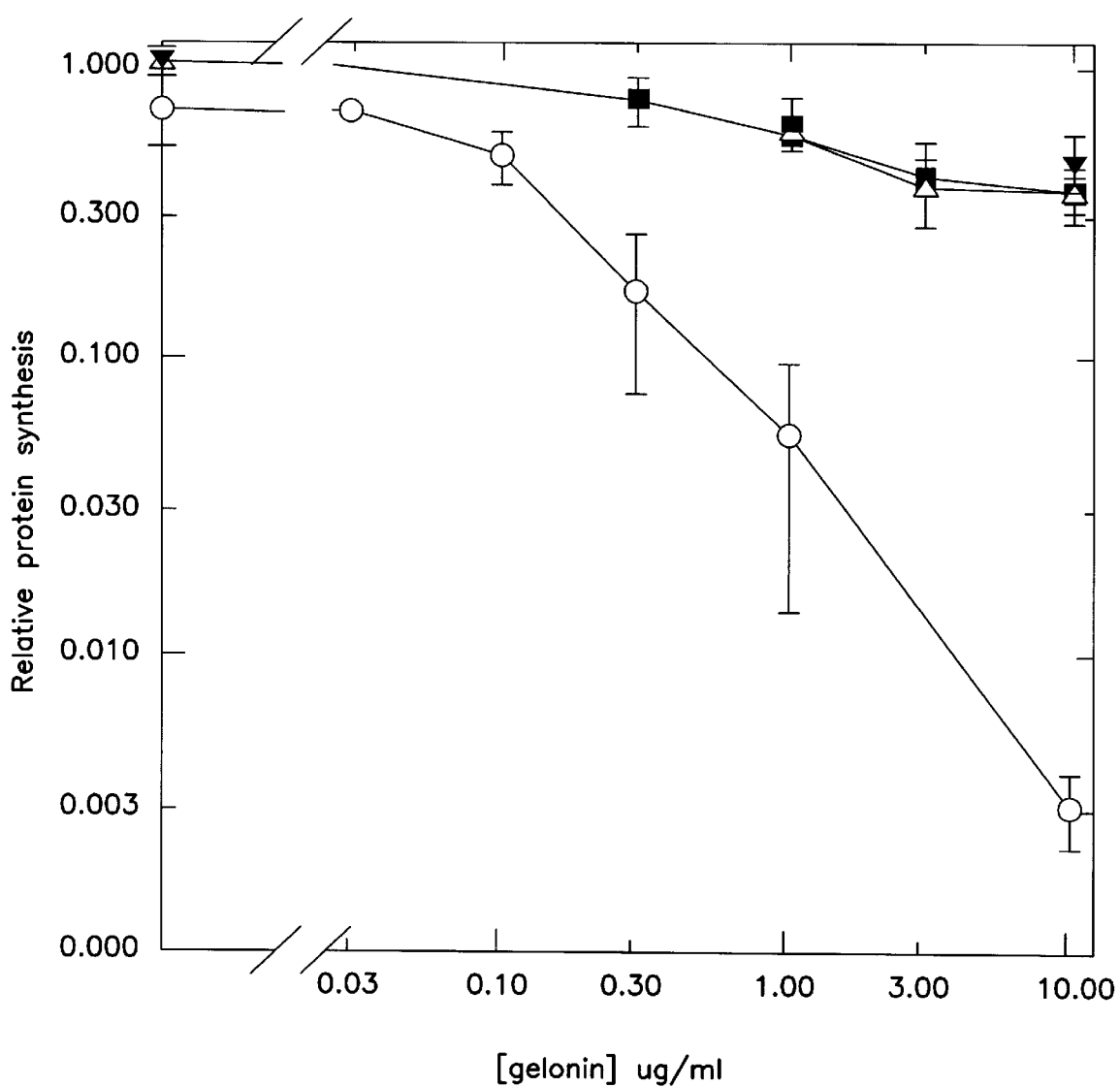
Figure 3:
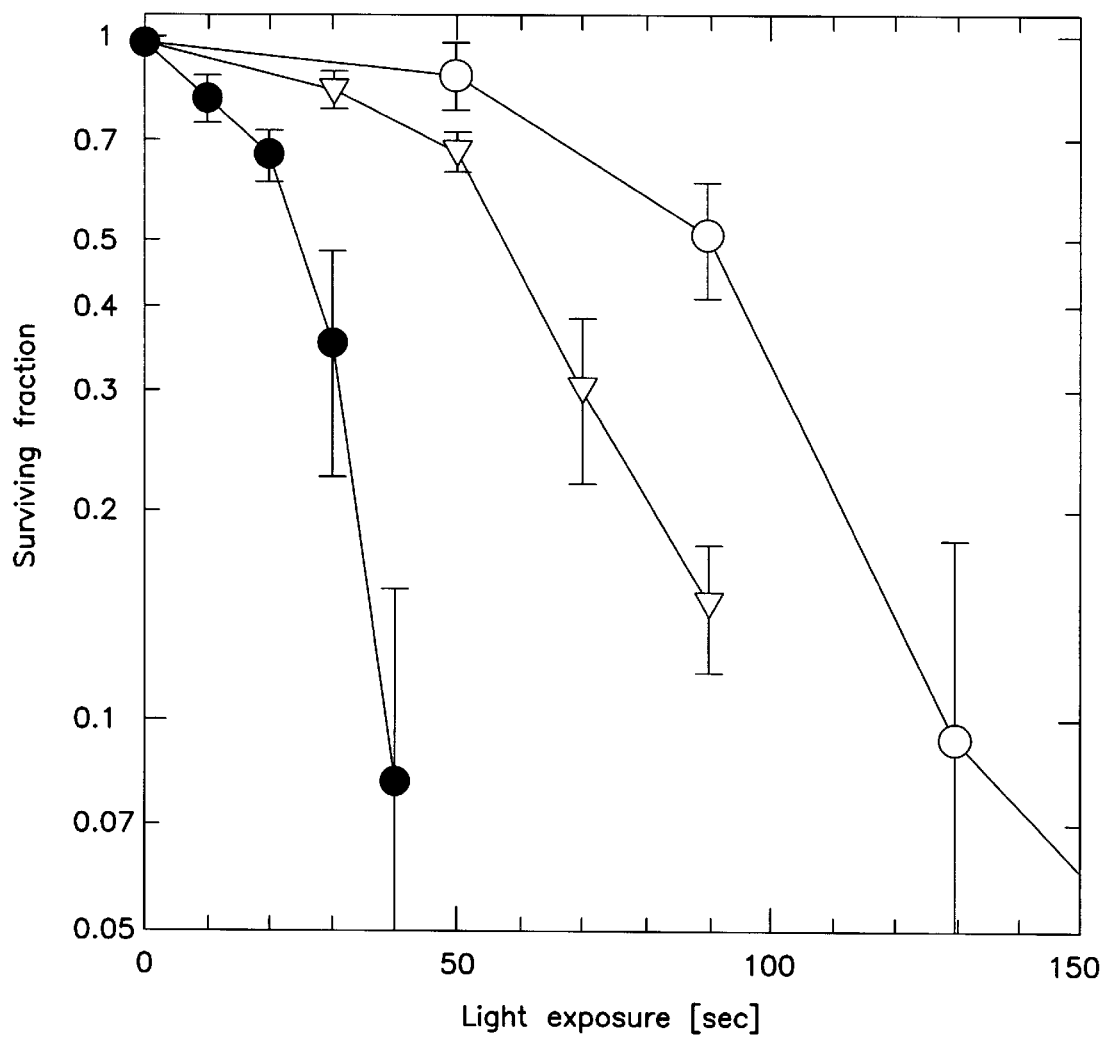
Figure 4:
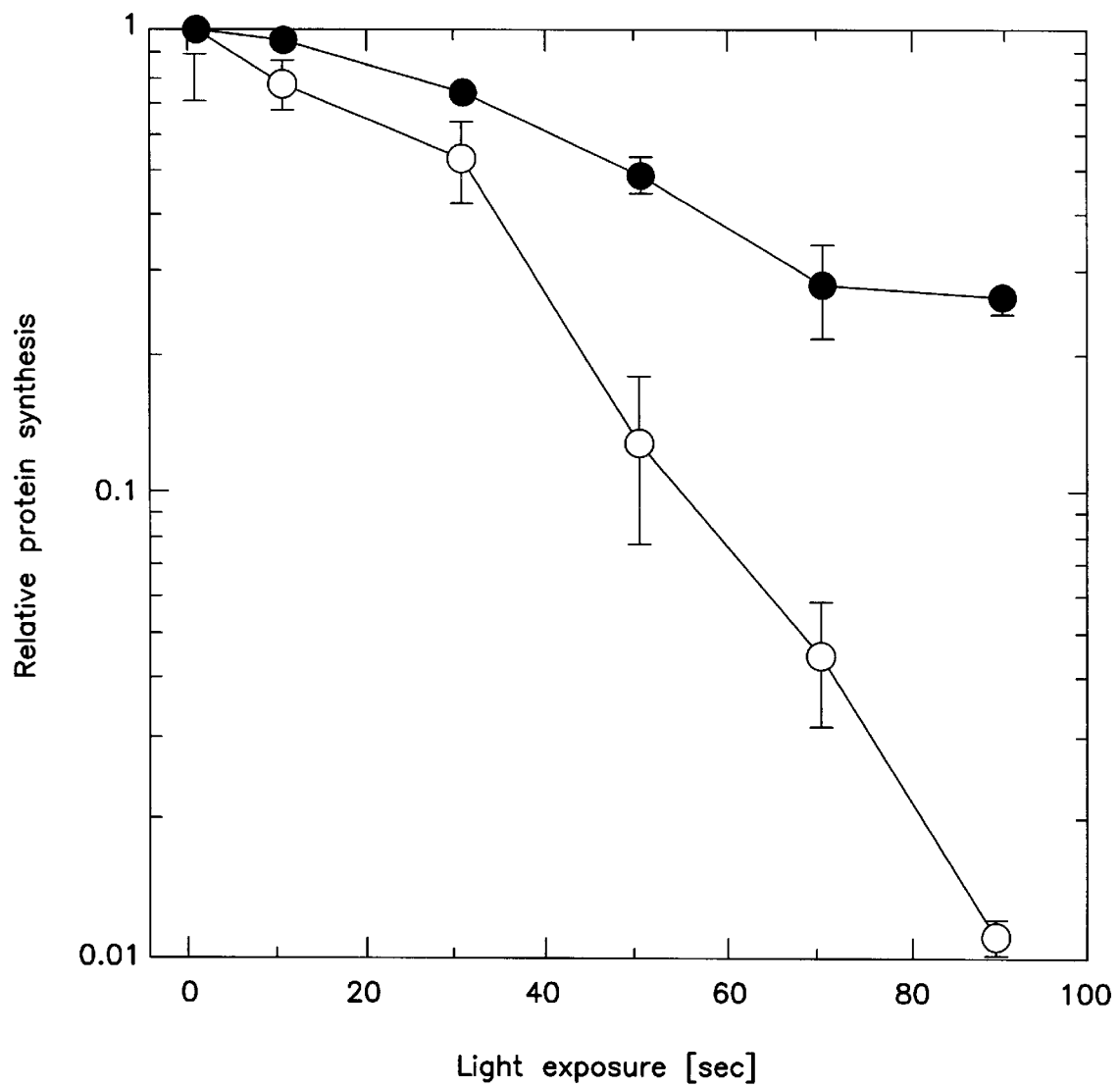

In the following the present invention is described in detail and illustrated by the figures, of which;

FIG. 1. represents illustration of how molecules can be introduced into the cellular cytosol by means of the present invention. The photosensitizer (S) and the molecules of choice (M) are endocytosed by the cells (I, illustrates the invagination of the plasma membrane initiating the endocytic process) and both substances end up in the same vesicles (II). When these vesicles are exposed to light, the membranes of the vesicles rupture and the contents are released (III);

FIG. 2. illustrates protein synthesis in NHIK 3025 cells after treatment with gelonin in the absence or presence of TPPS$_{2a}$ and 50 sec light exposure. Symbols: ○, TPPS$_{2a}$+ light; ●,–TPPS$_{2a}$–light; ▽,+TPPS$_{2a}$–light; ▼,–TPPS$_{2a}$+ light. The cells were treated with 3,2 $\mu$g/ml TPPS$_{2a}$ and the indicated concentration of gelonin overnight and in all cases given the same dose of light. Protein synthesis was measured by measuring incorporation of $^3$[H]leucine into proteins, 24 h after light exposure;

FIG. 3. shows dose-response curves for cells treated with TPPS$_{2a}$ and light only (○) or in combination with 0.2 $\mu$g/ml (▽) or 2.0 $\mu$g/ml gelonin as described FIG. 2; and FIG. 4. shows protein synthesis in NHIK 3025 cells after treatment with 3,2 $\mu$g/ml TPPS$_{2a}$ and light in the absence or presence of 0,2 $\mu$g/ml gelonin. Symbols: ○, TPPS$_{2a}$– gelonin; ○, TPPS$_{2a}$+gelonin. The cells were treated with TPPS$_{2a}$ in the absence or presence of gelonin overnight and exposed to the indicated doses of light. Protein synthesis was measured by measuring incorporation of $^3$[H]leucine into proteins.

Figure 5:
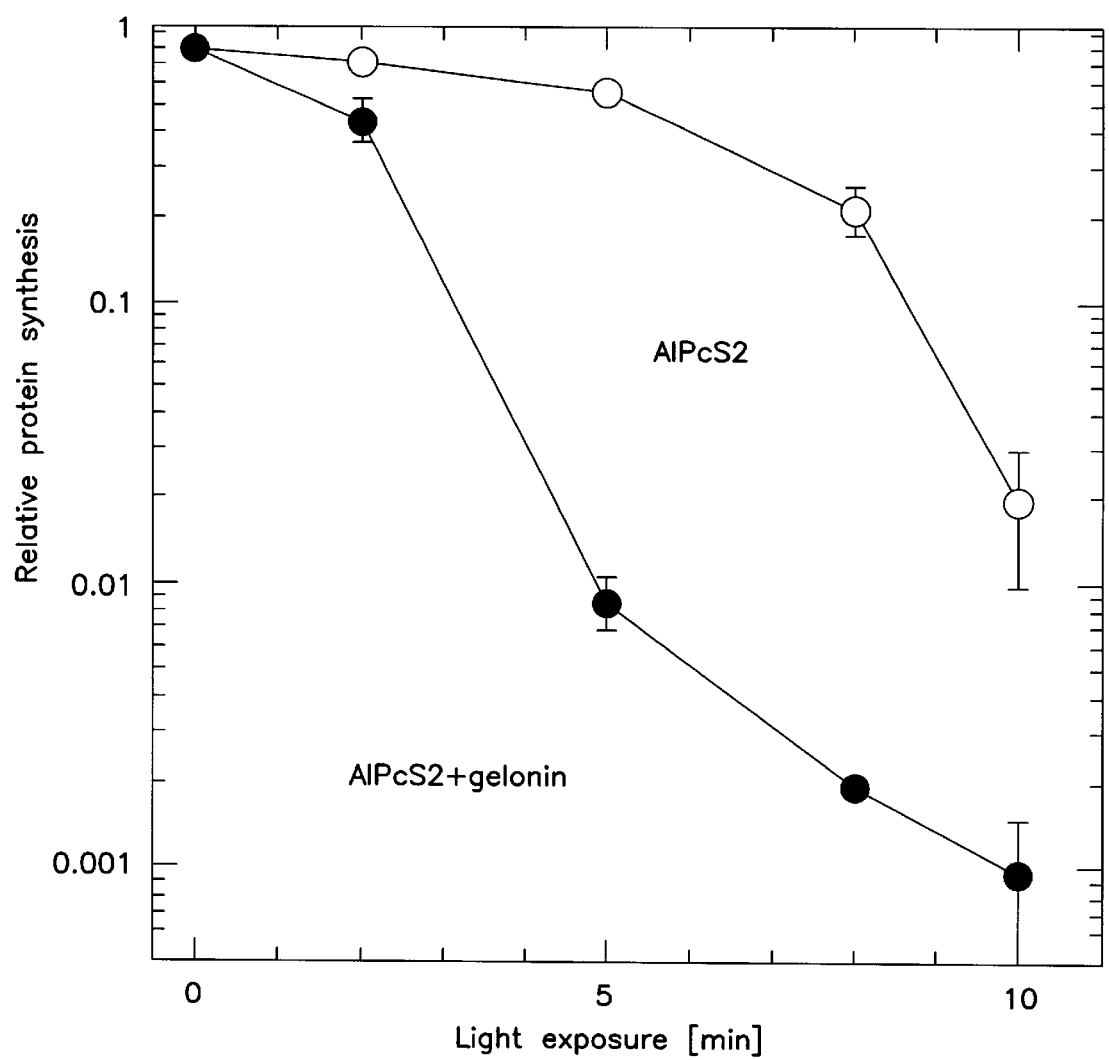

FIG. 5 illustrates protein synthesis in V79 cells after treatment with 25 µg/ml AlPcS$_2$ and light in the absence and presence of 1 µg/ml gelonin.

Figure 6:
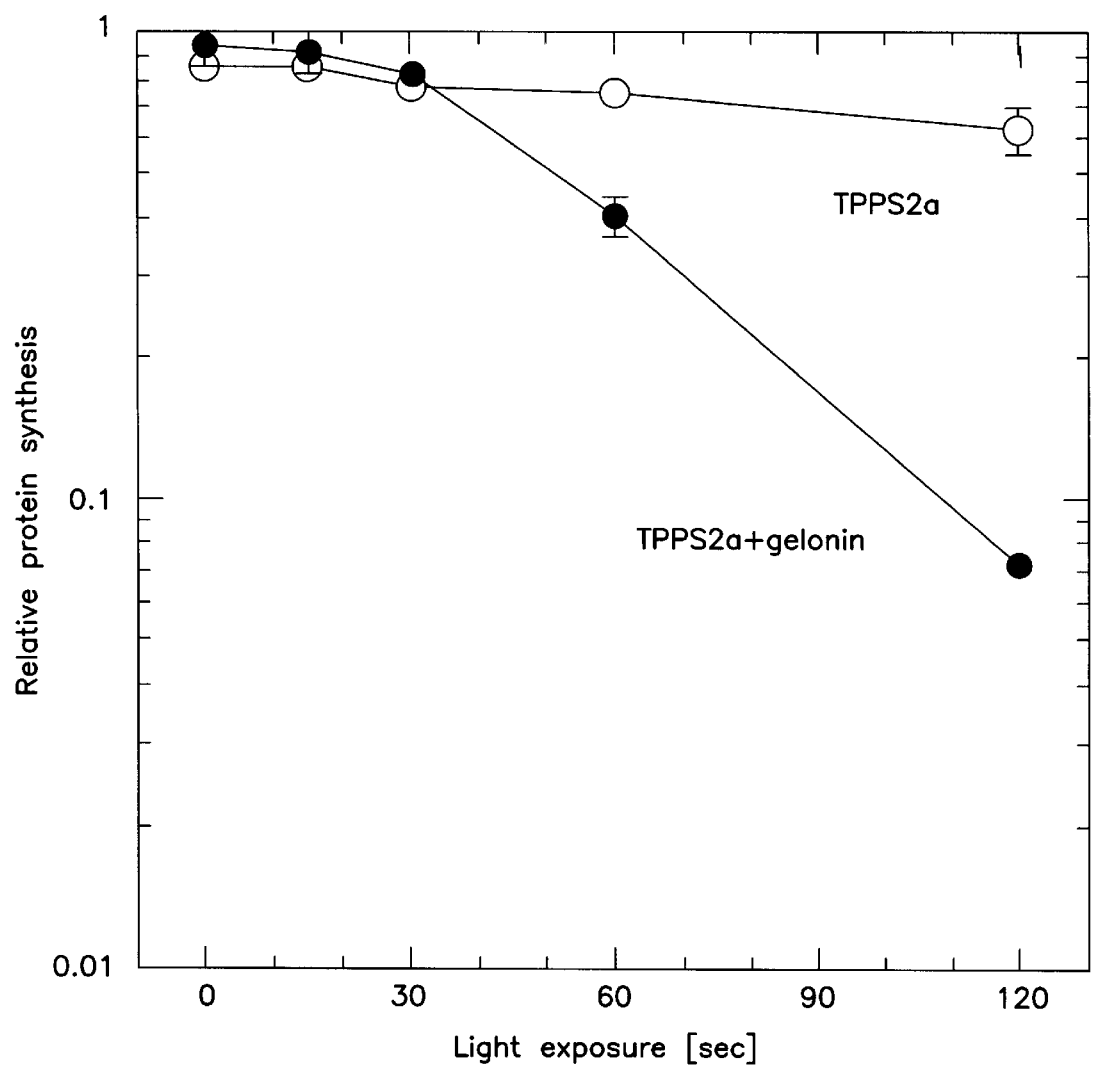
Figure 7:
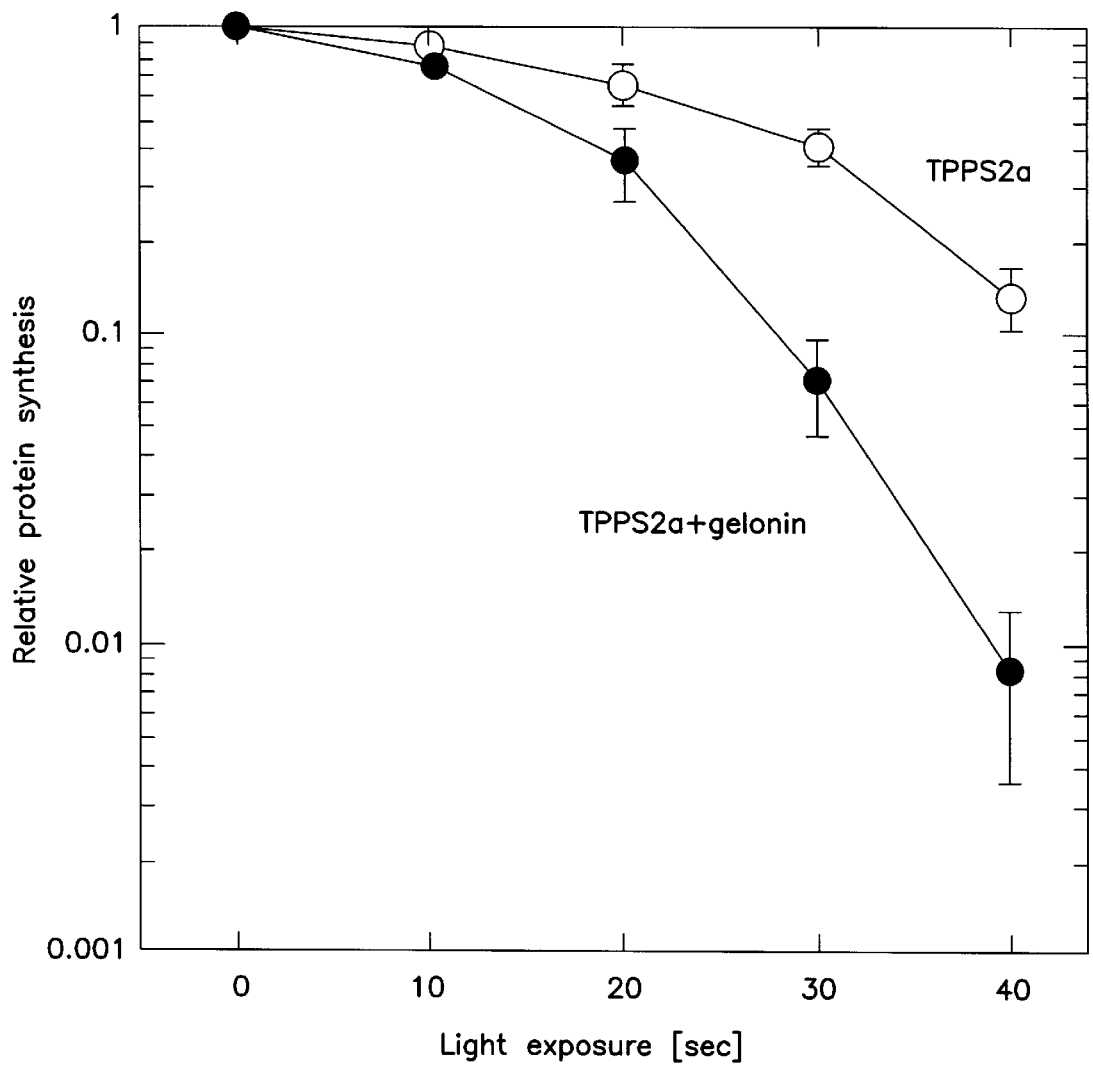
Figure 8:
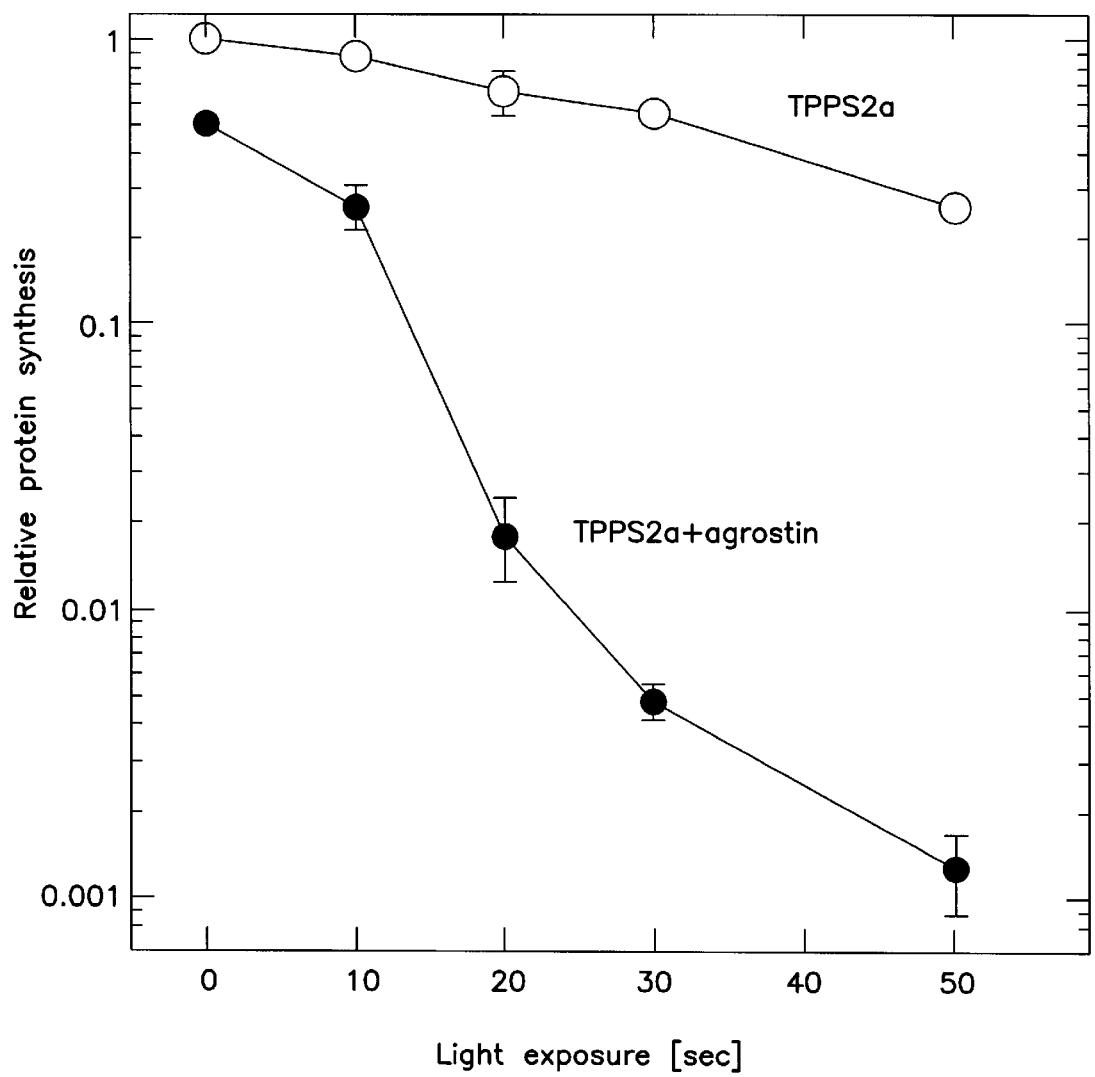
Figure 9:
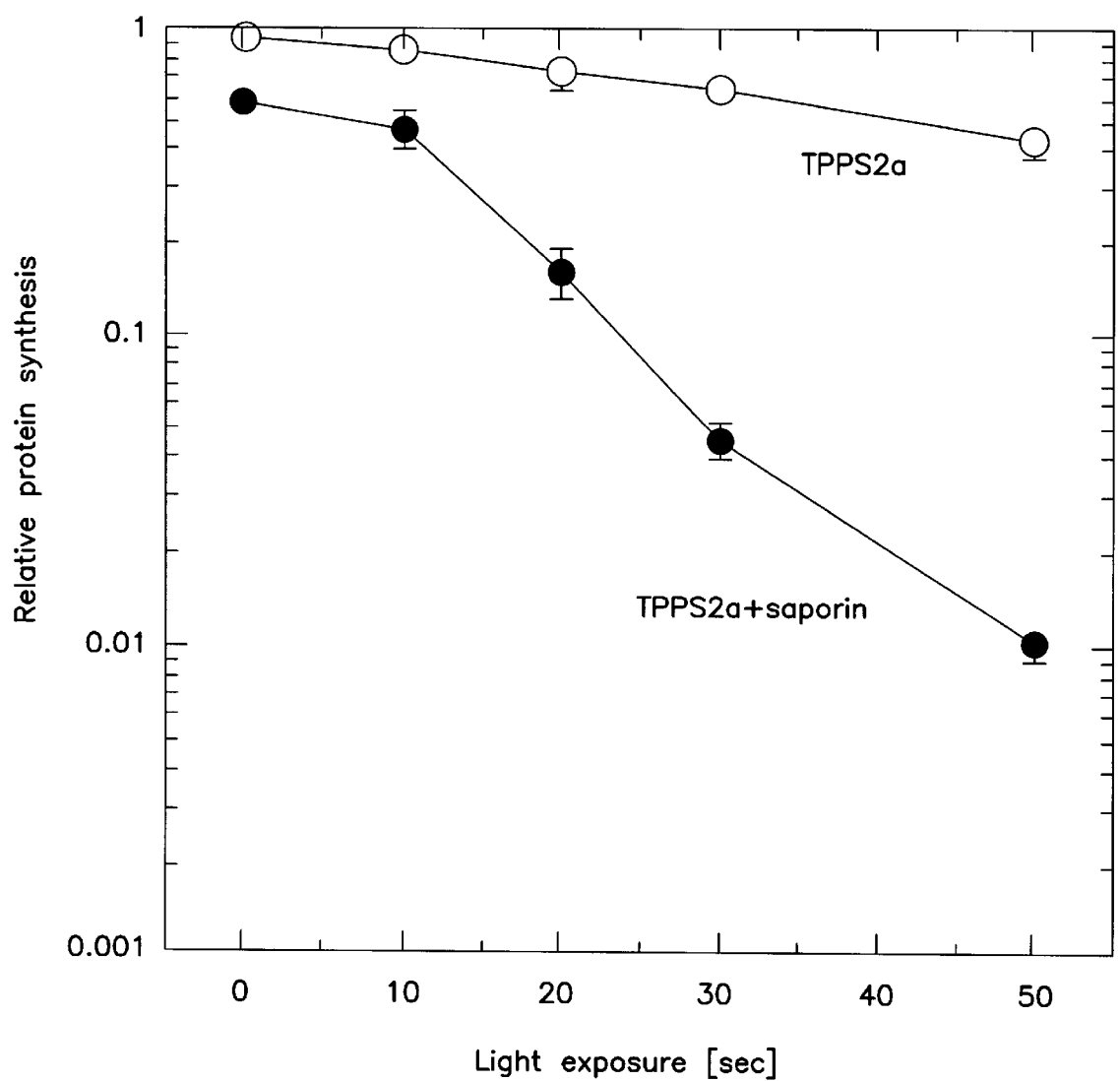
Figure 10:
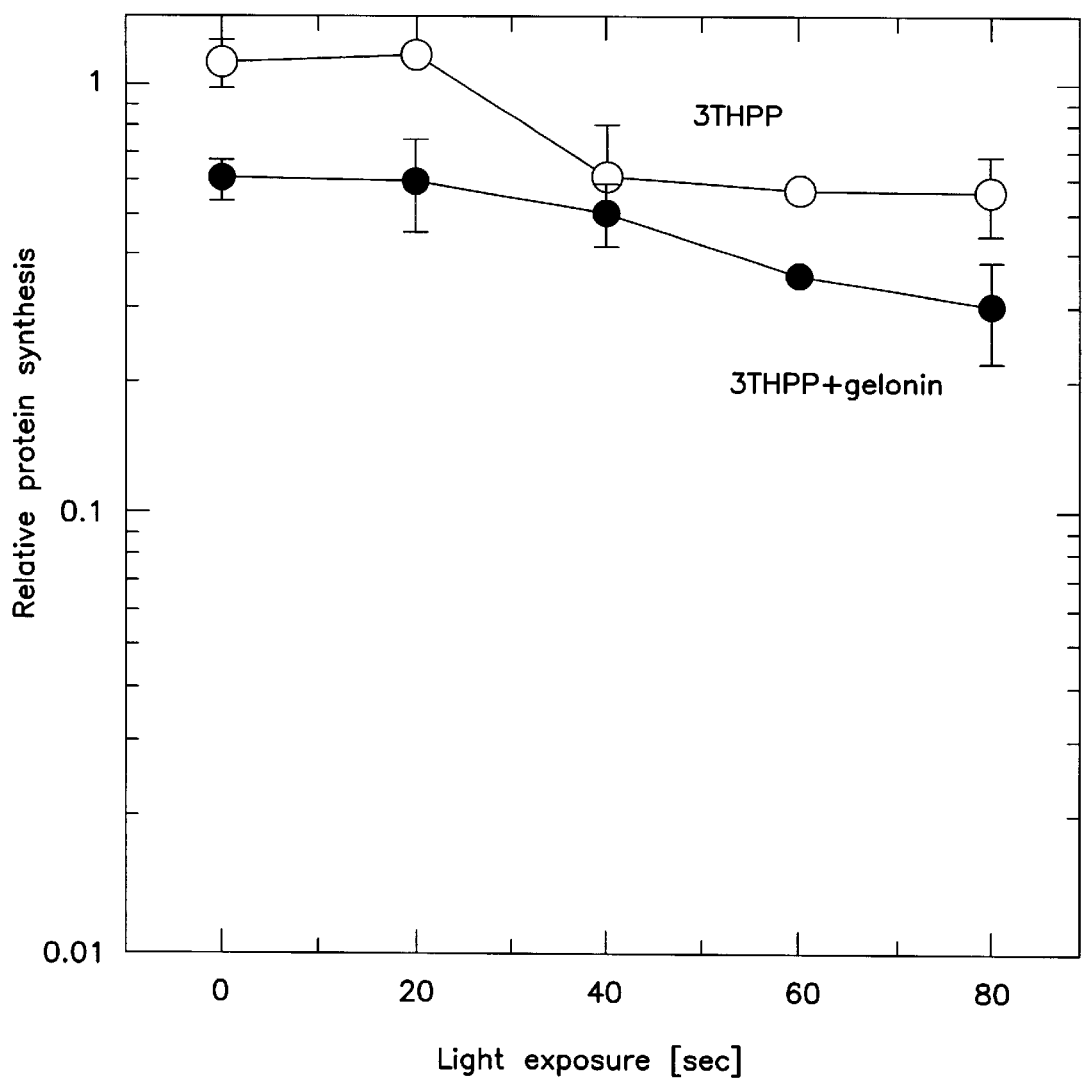
Figure 11:
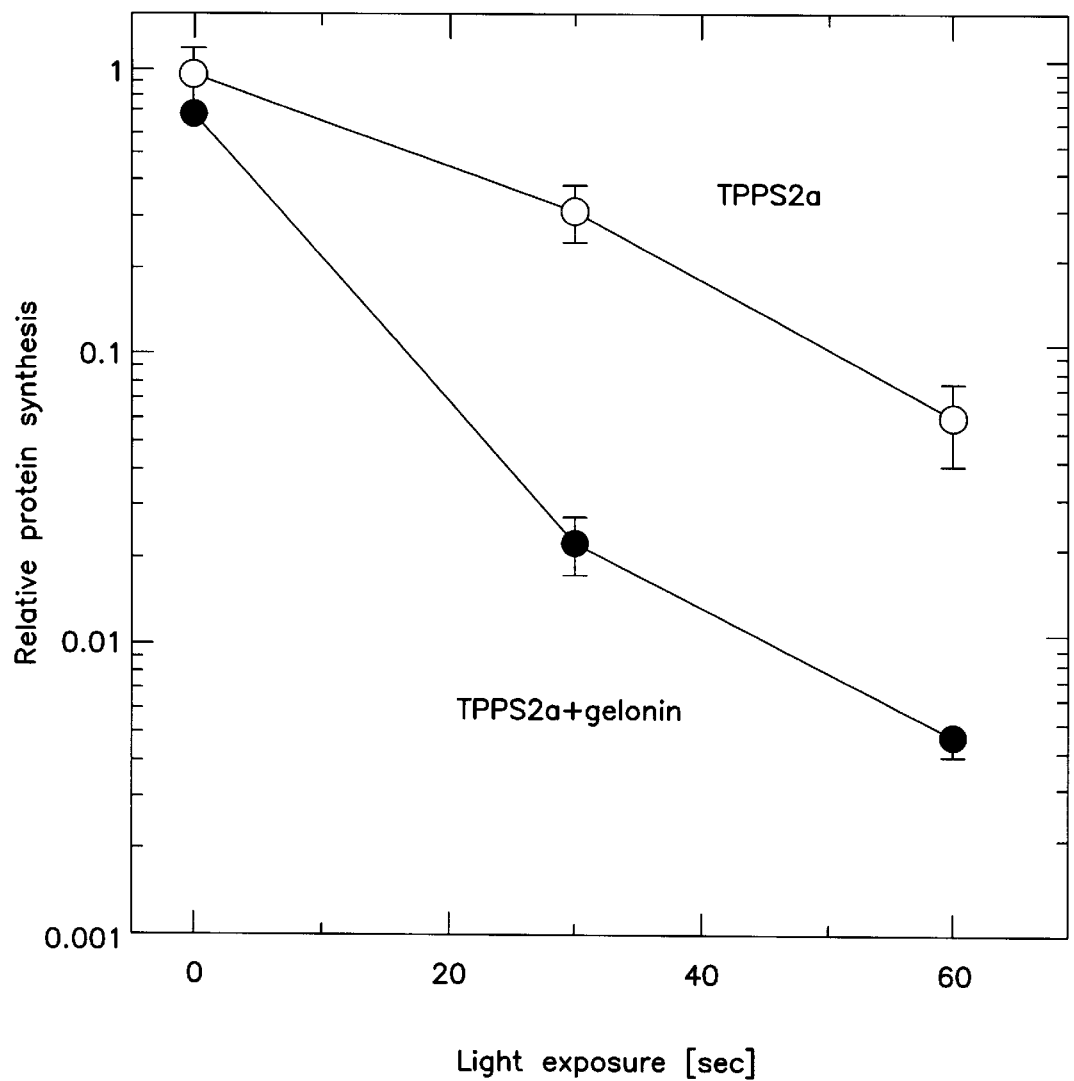
Figure 12:
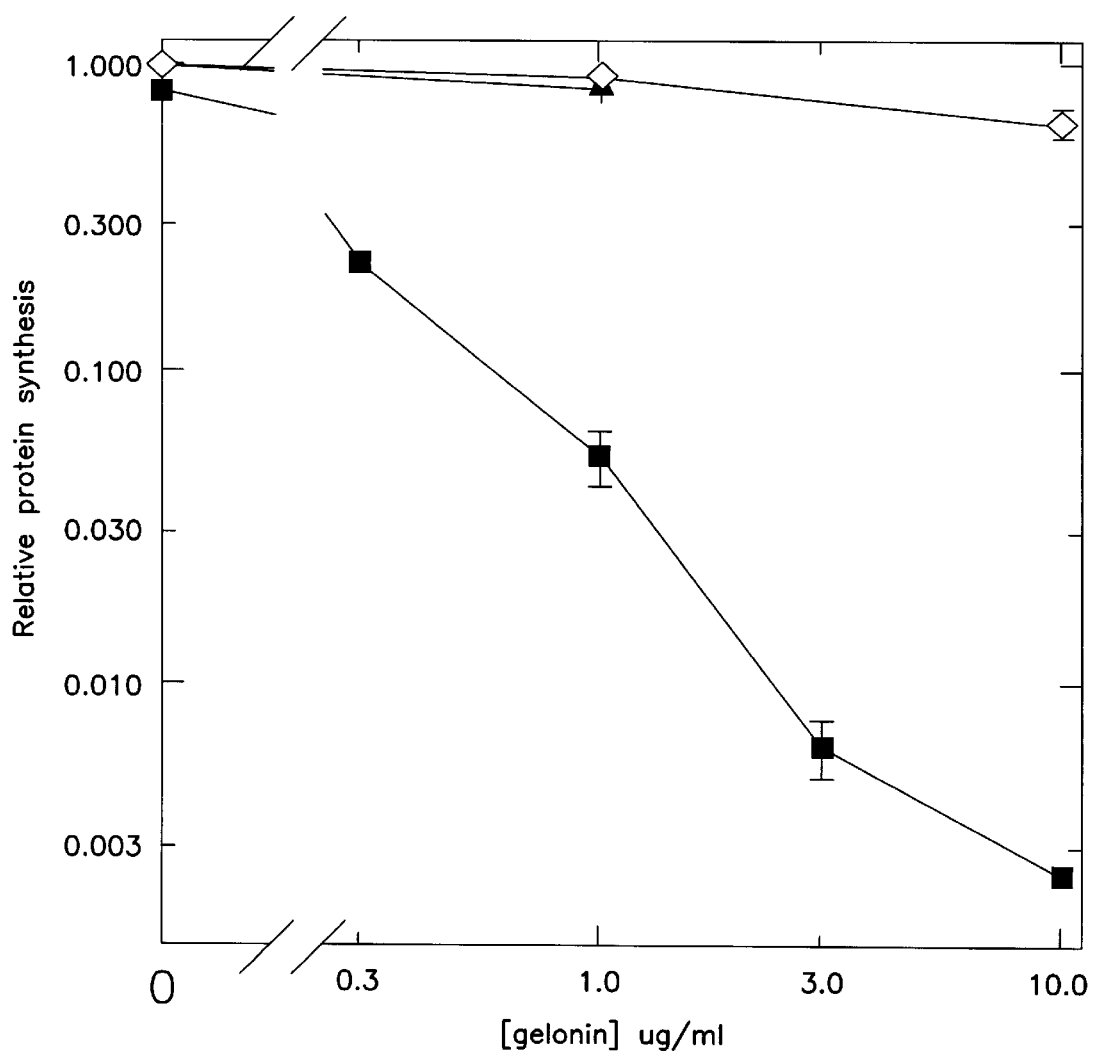
Figure 13:
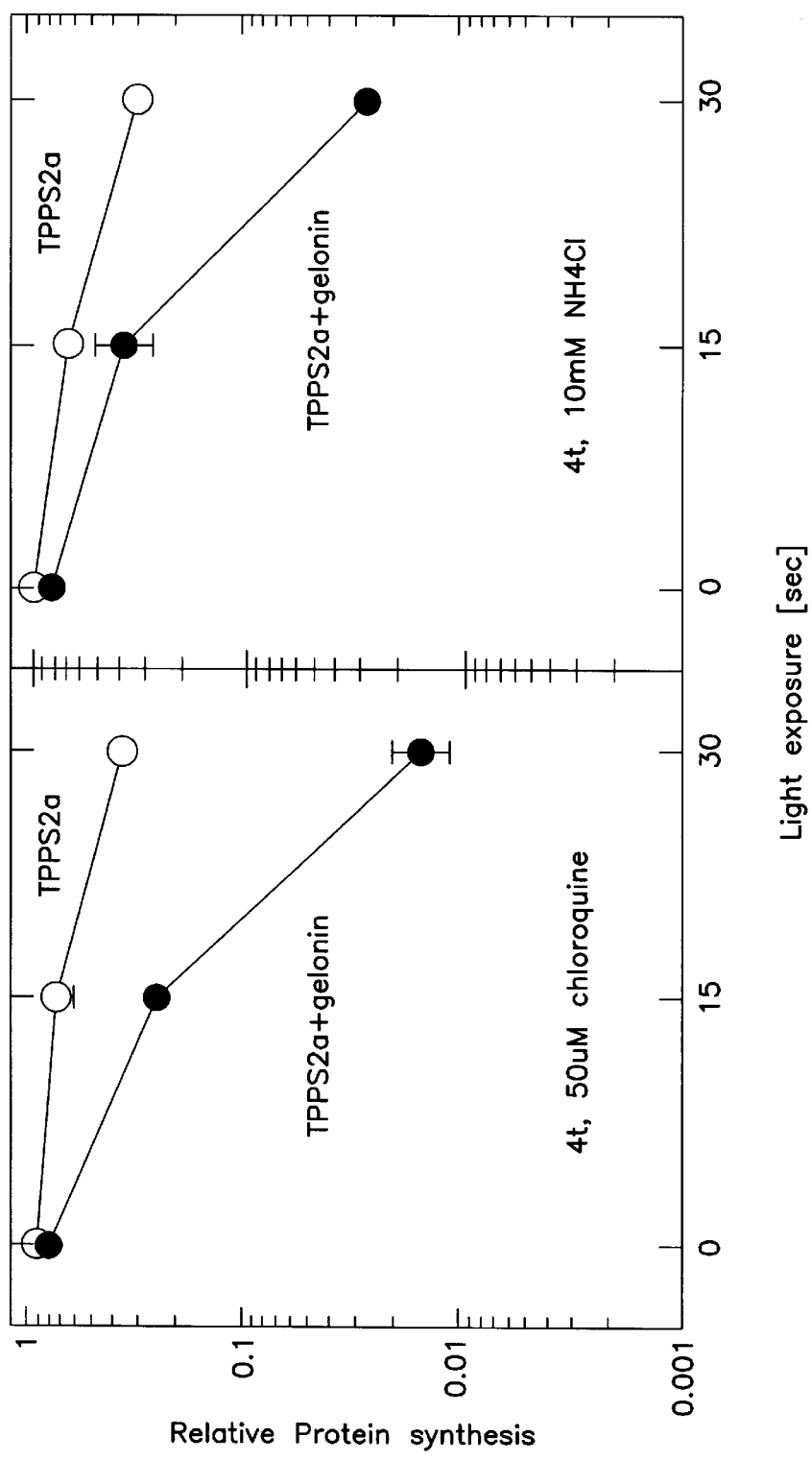

Symbols: ●Photosensitizer+toxin; ○photosensitizer,

FIG. 6 illustrates protein synthesis in H146 cells after treatment with 0,3 µg/ml TPPS$_{2a}$ and light in the absence and presence of 1 µg/ml gelonin. Symbols: as in FIG. 5, FIG. 7 illustrates protein synthesis in V79 cells after treatment with 1 µg/ml TPPS$_{2a}$ and light in the absence and presence of 1 µg/ml gelonin. Symbols: as in FIG. 5, FIG. 8 illustrates protein synthesis in NHIK3025 cells after treatment with 3,2 µg/ml TPPS$_{2a}$ and light in the absence and presence of 1 µg/ml agrostin. Symbols: as in FIG. 5, FIG. 9 illustrates protein synthesis in NHIK3025 cells after treatment with 3,2 µg/ml TPPS$_{2a}$ and light in the absence and presence of 1 µg/ml saporin. Symbols: as in FIG. 5, FIG. 10 illustrates protein synthesis in NHIK3025 cells after treatment with 0,25 µg/ml 3-THPP and light in the absence and presence of 1 µg/ml gelonin. Symbols: as in FIG. 5, FIG. 11 illustrates protein synthesis in COS-7 cells after treatment with 3 µg/ml TPPS$_{2a}$ and light in the absence and presence of 1 µg/ml gelonin. Symbols: as in FIG. 5, FIG. 12 illustrates protein synthesis in NHIK 3025 cells after treatment with gelonin in the absence or presence of TPPS4 and 50 sec light exposure. Symbols: ■TPPS$_4$+light; ▼−TPPS$_4$−light; ◇+RPPS$_4$ light. The cells were treated with 75 µg/ml TPPS$_4$ and the indicated concentration of gelonin overnight and in all cases given the same dose of light. Protein synthesis was measured by measuring incorporation of $^3$[H]leucine into proteins, 24 h after light exposure; and FIG. 13 illustrates protein synthesis in OHS cells after treatment with 3 µg/ml TPPS$_{2a}$ for 18 hours followed by 4 hours in the absence of TPPS$_{2a}$ and in the absence or presence of 3 µg/ml gelonin before exposure to light. The cells were incubated for the same 4 hours in 50 µM chloroquine or 10 mM NH$_4$Cl to inhibit lysosomal protein degration.

It is well documented that a number of drugs, including di- and tetrasulfonated aluminium phthalocyanine, sulfonated tetraphenylporphines (TPPS$_n$), nile blue, chlorin e$_6$ derivatives, uroporphyrin I, phylloerythrin and possibly hematoporphyrin and methylene blue is located in endosomes and lysosomes of cells in culture. This is in most cases due to endocytic activity. The inventors have shown that light exposure of cells containing photosensitizers in their lysosomes leads to a permeabilization of the lysosomes and release of the photosensitizer. In some cases, e.g. TPPS$_{2a}$ and TPPS$_1$, substantial amounts of lysosomal enzyme activities have been found in the cytosol after PDT, indicating that lysosomal contents can be released into the cytosol without losing their activity. This effect of photosensitizing dyes can be used to release endocytosed molecules from endosomes and lysosomes in general according to the present investigation.

The introduction of molecules into the cellular cytoplasm is achieved by first exposing the cells or tissue to a photosensitizing dye, the molecule(s) which one wants to deliver into the cytosol of the cells together with, or not carrier molecules and immunoglobins, all of which should preferentially localize in endosomes and/or lysosomes. Secondly, the cells or tissue is exposed to light of suitable wavelengths and energies inducing a photodynamic reaction. This photodynamic reaction will lead to disruption of lysosomal and/or endosomal membranes and the contents of these vesicles will be released into the cytosol.

The principles of the present invention are illustrated in FIG. 1. It is necessary that the photosensitizer and the molecule to be introduced into the cells are located in the same compartments. It should also be emphasized that externally added molecules may accumulate in intracellular compartments other than lysosomes and endosomes, e.g. Golgi apparatus and endoplasmic reticulum. In such cases, photosensitizing compounds located in the same compartments may in combination with light be used for the same purposes provided that the combination of light dosis and photosensitizing compound does not destroy the functionality of the cells.

The present invention is based on our in vitro demonstration, that a photosensitizer, for example TPPS$_{2a}$, (tetraphenylporphine with 2 sulfonate groups on adjacent phenyl groups) in combination with light can induce release of functionally intact lysosomal contents without killing a large fraction of the cells. The same effect may be obtained by using other photosensitizing compounds alone or associated with /linked to other molecules or particles used as vectors for directing the photosensitizers to endosomes/lysosomes or other intracellular compartments. Such vectors can be tissue or cell specific antibodies or other ligands that bind to the cell surface, thus increasing the uptake of the photosensitizer through receptor-mediated endocytosis. Another vector could be the use of reconstituted LDL-particles. These particles are also taken up by receptor-mediated endocytosis. The number of photosensitizer molecules per LDL particle and the binding to the LDL-particles can in this way be increased compared to prebinding to native LDL.

The present invention is not restricted to in vitro use, but may as well be used in vivo, either by in situ treatment or by ex vivo treatment followed by injection of the treated cells. The uptake into endosomes and lysosomes can be enhanced in the same manner as described above for in vitro treatment. All tissues can be treated as long as the photosensitizer is taken up by the target cells and the light can be properly delivered.

The present invention is based on both a photosensitizer and light. The light must be absorbed by the photosensitizer or indirectly induce an excited state of the photosensitizer. The wavelength region of use will therefore depend on the photosensitizer. The exposure light does not need to be monochromatic or collimated. Every light source emitting the appropriate wavelengths can be used.

Surprisingly the photodynamic action according to the present investigation seems to neutralize the potentially cytotoxic effect of releasing the lysosomal content. The present authors have thus established that lysosomal cathepsin is substantially inhibited by the photodynamic action of TPPS$_{2a}$ in a culture of NHIK 3025 cells. This was a surprising effect of the present invention and assists in maintaining the viability and functionality of the cells after transporting molecules into cytosol by disrupting endosomal/lysosomal membranes.

Examples of experimental and clinical utilization
1) Cancer treatment.

Several photosensitizers accumulate preferentially in neoplastic tissues, the selectivity for a tumor over the surrounding tissue being usually a factor of 2–3, but this factor may in some cases, such as for brain tissues, be higher, i.e. up to 30. Molecules which may be of clinical interest for treatment of cancer, but are restricted by a low or no uptake into the cytosol can be introduced into the cytosol by means of the present invention. Gelonin, as exemplified below, is an example of such a molecule. Several other molecules, either alone or linked to other molecules (e.g. antibodies, transferrin, photosensitizers, apoB on reconstituted LDL-particles) can be used. The advantage of such a combination treatment would be 1) enhanced cytotoxic effect in deeper layers of the tumor tissues since low and subtoxic doses of light are sufficient for disruption of lysosomes and endosomes; 2) enhanced specificity of the toxin since PDT is only given to the area of tumor localization.

2) Gene therapy

Gene therapy, i.e. therapeutic transfer of genes to the patients cells, is promising as a method for treating many genetic disorders such as cancer, cystic fibrosis, cardiovascular diseases and many other diseases. The main problem today is the transfection which must occur in vivo or in some cases can be performed ex vivo. Today, the most frequently used vector, i.e. the structure that helps delivering the DNA molecules into the cells, is different types of viruses, especially retro- and adenoviruses. The drawbacks of such methods are low stability of the vector, limited specificity, low yield and introduction of virus-DNA into human cells.

DNA, either as antisense DNA or whole genes, can be introduced into cells by the aid of photochemically induced disruption of endosomes and/or lysosomes. The treatment can be performed in vivo.

3) Experimental utilization

The present invention can be used to introduce a wide variety of molecules into cells in culture, e.g., genes, antibodies, manipulated proteins and compounds usually not permeable to the plasma membrane.

The present invention is further illustrated by the following non-limiting examples.

EXAMPLE 1

This example demonstrates that photodynamic treatment releases a protein synthesis inhibiting compound into the cytosol.

A number of plant toxins kill cells by entering the cytosol and inactivating enzymatically the ribosomal function. The most cytotoxic plant proteins consist of 2 polypeptide chains, A and B, linked together by disulfide bridges. The function of chain B is to bind the protein to the surface of the cells, while chain A contains the enzymatic activity. Gelonin is a plant toxin which efficiently inhibits protein synthesis in cell-free systems, but has little or no effect on intact cells. The low cytotoxic effect on intact cells is probably due to the lack of a B chain in gelonin.

NHIK 3025 cells were incubated with TPPS$_{2a}$ (Formula I) and gelonin, separately or together for 18 h, followed by 1 h in TPPS$_{2a}$ and gelonin-free medium before the cells were exposed to light. Protein synthesis was measured 24 h after exposure to light. The photodynamic treatment, which kills 10–20% of the cells alone, reduced the protein synthesis by 30–40% (FIG. 2). As seen in FIG. 2 gelonin alone in the presence or absence of light inhibits protein synthesis to some extent. However, protein synthesis can be completely inhibited by combining PDT and gelonin with an IC$_{50}$=0.2 μg/ml gelonin. Thus in absence of the photodynamic treatment the gelonin essentially did not enter cytosol. This example indicates that TPPS$_{2a}$ and light can be used to introduce functionally intact macromolecules into the cellular cytosol.

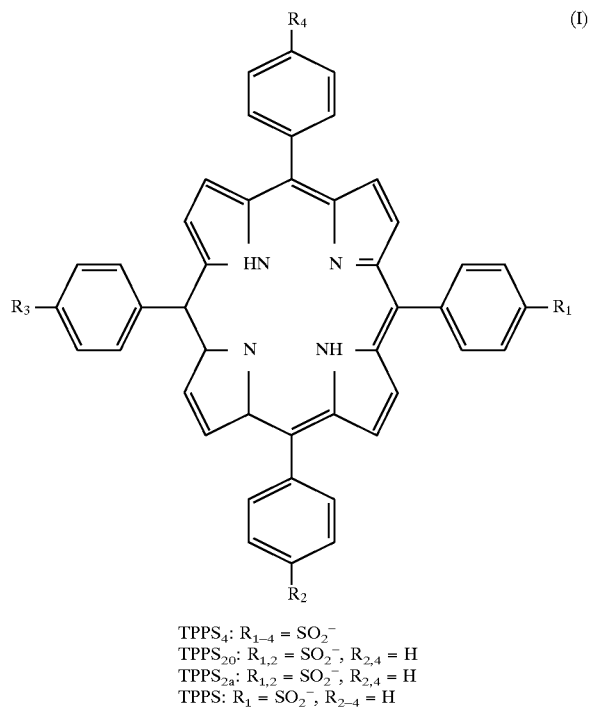

TPPS$_4$: R$_{1-4}$ = SO$_2^-$
TPPS$_{2o}$: R$_{1,2}$ = SO$_2^-$, R$_{2,4}$ = H
TPPS$_{2a}$: R$_{1,2}$ = SO$_2^-$, R$_{2,4}$ = H
TPPS: R$_1$ = SO$_2^-$, R$_{2-4}$ = H

EXAMPLE 2

This example illustrates how the dose of light (with the wavelength which is absorbed by the dye) can be used to decide the size of the surviving cell fraction.

NHIK 3025 celles were incubated with TPPS$_{2a}$ and gelonin according to the design of Example 1.

Clonogenic survivial of the cells was measured 24 h after exposure to light. As illustrated in FIG. 3 virtually all cells were killed with TPPS$_{2a}$ and light when the light exposure was increased. This is in accordance with prior art regarding killing unwanted cells with PDT. When gelonin is added the survival rate drops due to the inhibiting effect of gelonin on protein synthesis, showing that gelonin now is released in the cytosol. Increased concentration of added gelonin leads to more gelonin in the cytosol, as indicated by an increased sensitivity of the cells to photo inactivation.

The present invention thus offers the possibility to set a level of survival in each case and select a combination of photosensitizing compound and light exposure which will keep the wanted fraction of cells alive.

EXAMPLE 3

This example illustrates how changing light doses control the amount of gelonin released in the cytosol, as determined by the relative protein synthesis.

NHIK 3025 cells were incubated with TPPS$_{2a}$ and gelonin according to the design of Example 1.

FIG. 4 shows that light doses above the toxic dose of 50 sec increased the gelonin fraction in cytosol as determined by the relative protein synthesis.

Example 4–11 demonstrates use of the method according to the invention on different cell lines and with different photosensitizers and toxins. The intracellular location of the photosensitizers are lysosomal (TPPS$_4$, TPPS$_{2a}$, AlPcS$_{2a}$) and extralysosomal (3-THPP). The following abbrevations are used: AlPcS$_{2a}$ for aluminium phtalocyanine with 2 sulfonate groups on adjacent phenyl rings; TPPS$_4$ for meso-tetraphenylporphine with 4 sulfonate groups; TPPS$_{2a}$ for meso-tetraphenylporphine with 2 sulfonate groups on adjacent phenyl rings; 3-THPP for tetrahydroxylphenyl porphine. The used cell lines are carcinoma cells in situ from human cervix (NHIK 3025), Chinese hamster lung fibroblasts (V 79), SV40-transformed African Green monkey kidney (CV1-simian fibroblasts-like cells) (Cos-7) human osteosarcoma cells (OHS) and small cell lung cancer cells (H146). All experiments were designed as in Example 1.

EXAMPLE 4

This example relates to use of the photosensitizer AlPcS$_{2a}$ in V79 cells with/without gelonin as the toxin (FIG. 5). By selecting a specific light dose (irradiation time) it is demonstrated that, without the toxin very little cell damage is produced as illustrated by the small reduction in protein synthesis, while with gelonin the protein synthesis is profoundly reduced. This shows the transport of gelonin molecules into cell cytoplasma via lysosomes without essentially damaging the cells even though the intracellular localization of AlPcS$_{2a}$ is lysosomal (Moan, J., Berg, K., Anholt, H. and Madslien, K. (1994). Sulfonated aluminium phtalocyanines as sensitizers for photochemotherapy. Effects of small light doses on localization, dye fluorescence and photosensitivity in V79 cells. Int. J. Cancer 58: 865–870).

EXAMPLE 5

This example demonstrates transport of the toxin gelonin into H146 cells without essentially affecting the viability of the cells. (FIG. 6). TPPS$_{2a}$ is known to be lysosomal located in the cell. (Berg, K., Western, A., Bommer, J. and Moan, J. (1990) Intracellular localisation of sulfonated meso-tetraphenylporphines in a human carcinoma cell line. Photochem. Photobiol. 52:481–487; Berg, K., Madslien, K., Bommer J. C., Oftebro, R., Winkelman, J. C. and Moan, J. (1991). Light induced relocalization of sulfonated meso-tetraphenylporphines in NHIK 3025 cells and effects of dose fractionation. Photochem. Photobiol. 53:203–210; Berg, K and Moan, J. (1994) Lysosomes as photochemical targets. Int. J. Cancer. 59:814–822).

EXAMPLE 6

This example demonstrates the method according to the invention in V79 cells using TPPS$_{2a}$ as photosensitizer (FIG. 7).

EXAMPLE 7

This example demonstrates transport into NHIK 3025 cells of the toxin agrostin using the photosensitizer TPP$_{2a}$ (FIG. 8).

EXAMPLE 8

This example demonstrates transport of the toxin saporin into NHIK 3025 cells using TPP$_{2a}$ (FIG. 9).

EXAMPLE 9

This is a comparison example demonstrating that when a photosensitizer (3-THPP) which does not enter endocytic vesicles (i.e. endosomes and lysosomes) (Peng, Q., Danielsen, H. E. and Moan, J. (1994) Potent photosensitizers for photodynamic therapy of cancer: Applications of confocal laser scanning microscopy for fluorescence detection of photosensitizing fluorophores in neoplastic cells and tissues. In: Proceedings of Microscopy, Holography, and Interferometry in Biomedicine. SPIE Vol. 2083:71–82), there is no significant difference between the protein synthesis effect of 3THPP with or without gelonin (FIG. 10). Thus gelonin is not transported into the cytosol of the cells.

EXAMPLE 10

This example demonstrates the transport of gelonin into COS-7 cells by using TPPS$_{2a}$ according to the invention (FIG. 11).

EXAMPLE 11

This example demonstrates the transport of gelonin into OHS cells by using TPPS$_{2a}$ according to the invention. (FIG. 13). In this cell line there is a considerable protein degradation in the lysosomes, which in the present example is inhibited by incubating the cells for 4 hours in either 50 $\mu$M chloroquine or 10 mM NH$_4$Cl.

EXAMPLE 12

Similar to example 1 this example demonstrates transport of gelonin into NHIK 3025 cells as a function of the gelonin concentration when the cells were incubated with TPPS$_4$ and different concentrations of gelonin, and exposed to light (FIG. 12). When the cells were incubated with gelonin alone and exposed to light, or incubated with TPPS4 and gelonin without exposure to light, no transport of gelonin into the cells was obtained.

The examples demonstrate that different molecules can be introduced into the cells cytosol in a wide variety of cells using different photosensitizers and doses of light. Exogenous molecules can be introduced to the cellular cytosol after doses of photosensitizers and light which do not kill the cells, as long as the molecules to be introduced and the photosensitizers are transported to the same cellular compartments. The photochemical effect on a biological compartment is dependent upon the amount of photosensitizers in that compartment, the dose of light applied and the spectral properties of the light source. The best way to evaluate photochemical effects on cells in culture is therefore to measure cell survival 24 hours or more after treatment. There is a good correlation between the effect on cell killing and inhibition of protein synthesis 24 hours after treatments as presented above (data not shown).

We claim:

1. A method for introducing a molecule of interest into the cytosol of a living cell, comprising:
    a) delivering a photosensitizing compound, the molecule of interest, and a carrier molecule to the cell, wherein each are taken up into an intracellular compartment of the cell;
    b) irradiating the cell with light of a suitable wavelength to activate the photosensitizing compound so that the membrane surrounding the intracellular compartment is disrupted, releasing the molecule of interest into the cytosol of the cell without killing the cell.

2. The method according to claim 1 wherein the molecule of interest is DNA, an oligonucleotide, mRNA, antisense DNA, a sugar, a protein, a peptide, a membrane impermeable molecule, or a covalently or noncovalently bonded combination thereof.

3. The method according to claim 1, wherein the molecule of interest is gelonin, saporin, agrostin, or a combination thereof.

4. The method according to claim 1, wherein the photosensitizing compound is a porphyrin, a phthalocyanine, a purpurin, a chlorin, a benzoporphyrin, a napthalocyanine, a cationic dye, a tetracycline, or a lysosomotropic weak base or derivative thereof.

5. The method according to claim 4, wherein the photosensitizing compound is tetraphenyl porphine with 2 sulfonate groups on adjacent phenyl groups (TPPS$_{2a}$), meso-tetraphenyl porphine with 4 sulfonate groups (TPPS$_4$), or aluminum phthalocyanine with 2 sulfonate groups on adjacent phenyl rings (AlPcS$_2$) or a combination thereof.

6. The method according to claim 1, further comprising providing a vector molecule which facilitates the uptake of either the photosensitizing compound or the molecule of interest which is to be released into the cytosol.

7. The method according to claim 1, wherein the method is applied to a plurality of cells and wherein the step of irradiating includes selecting a light dose and wavelength and a photosensitizing compound so that after the step of irradiation, a portion of the living cells are killed.

* * * * *

UNITED STATES PATENT AND TRADEMARK OFFICE
CERTIFICATE OF CORRECTION

PATENT NO. : 5,876,989
DATED : March 2, 1999
INVENTOR(S) : Kristian Berg, Kristen Sandvig and Johan Moan It is certified that error appears in the above-identified patent and that said Letters Patent is hereby corrected as shown below:

Column 2,
Line 62, "O" should read -- ● --

Signed and Sealed this

Eighteenth Day of January, 2005

JON W. DUDAS
*Director of the United States Patent and Trademark Office*